United States Patent
Kim

(10) Patent No.: US 10,052,178 B2
(45) Date of Patent: Aug. 21, 2018

(54) IMPLANT FIXTURE

(71) Applicant: TRUABUTMENT KOREA, INC., Gyeonggi-do (KR)

(72) Inventor: Haeng Oh Kim, Busan (KR)

(73) Assignee: TRUABUTMENT KOREA, INC., Gyeonggi-do (KR)

( * ) Notice: Subject to any disclaimer, the term of this patent is extended or adjusted under 35 U.S.C. 154(b) by 0 days.

(21) Appl. No.: 15/371,196

(22) Filed: Dec. 6, 2016

(65) Prior Publication Data
US 2018/0092717 A1  Apr. 5, 2018

(30) Foreign Application Priority Data
Oct. 5, 2016 (KR) .......................... 10-2016-128462

(51) Int. Cl.
*A61C 8/00* (2006.01)
(52) U.S. Cl.
CPC .......... *A61C 8/0025* (2013.01); *A61C 8/0037* (2013.01)
(58) Field of Classification Search
CPC .... A61C 8/0022; A61C 8/0024; A61C 8/0025
See application file for complete search history.

(56) References Cited

U.S. PATENT DOCUMENTS

| | | | | |
|---|---|---|---|---|
| 5,088,926 A * | 2/1992 | Lang | .................... | A61C 8/0022 433/173 |
| 5,312,256 A * | 5/1994 | Scortecci | ............. | A61C 8/0022 433/173 |
| 5,702,445 A * | 12/1997 | Brånemark | ........ | A61B 17/8625 411/387.3 |
| 7,677,891 B2 * | 3/2010 | Niznick | ............... | A61C 8/0022 433/174 |
| 2013/0011811 A1 * | 1/2013 | Gourlaouen-Preissler | .............. | A61C 8/0012 433/173 |
| 2013/0090696 A1 * | 4/2013 | Chiquillo Perez | ... | A61C 8/0022 606/300 |
| 2014/0106305 A1 * | 4/2014 | Jacoby | ................. | A61C 8/0006 433/174 |

FOREIGN PATENT DOCUMENTS

WO  WO 2015/125139 A2 *  8/2015

* cited by examiner

*Primary Examiner* — Ralph Lewis
(74) *Attorney, Agent, or Firm* — Moser Taboada

(57) ABSTRACT

Provided is an implant fixture.
The fixture includes a first area portion including a plurality of first screw portions configured to correspond to a cortical bone during implantation in a bone tissue and have a first ridge portion and a first bottom portion which are formed to have a spiral shape and alternately disposed in a direction of a central axis, and a plurality of non-screw portions provided between adjacent first screw portions and including a continuous surface having a smaller radius at a terminal end of a first screw portion of one side than a radius of the first bottom portion with respect to the central axis, wherein the radius gradually increases toward a beginning end of a first screw portion of another side, and a second area portion positioned below the first area portion and configured to correspond to a cancellous bone of the bone tissue during the implantation in the bone tissue.

11 Claims, 7 Drawing Sheets

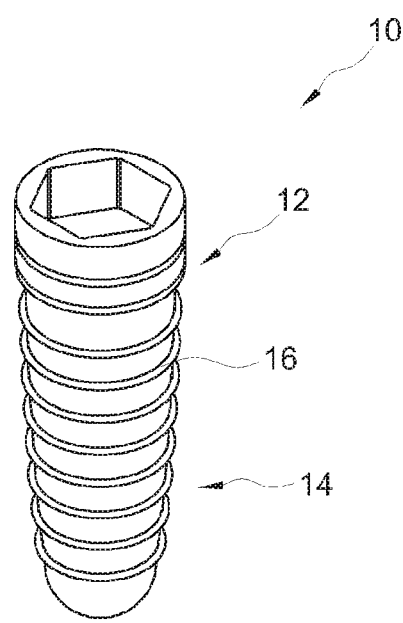
-PRIOR ART-
[FIG. 1]

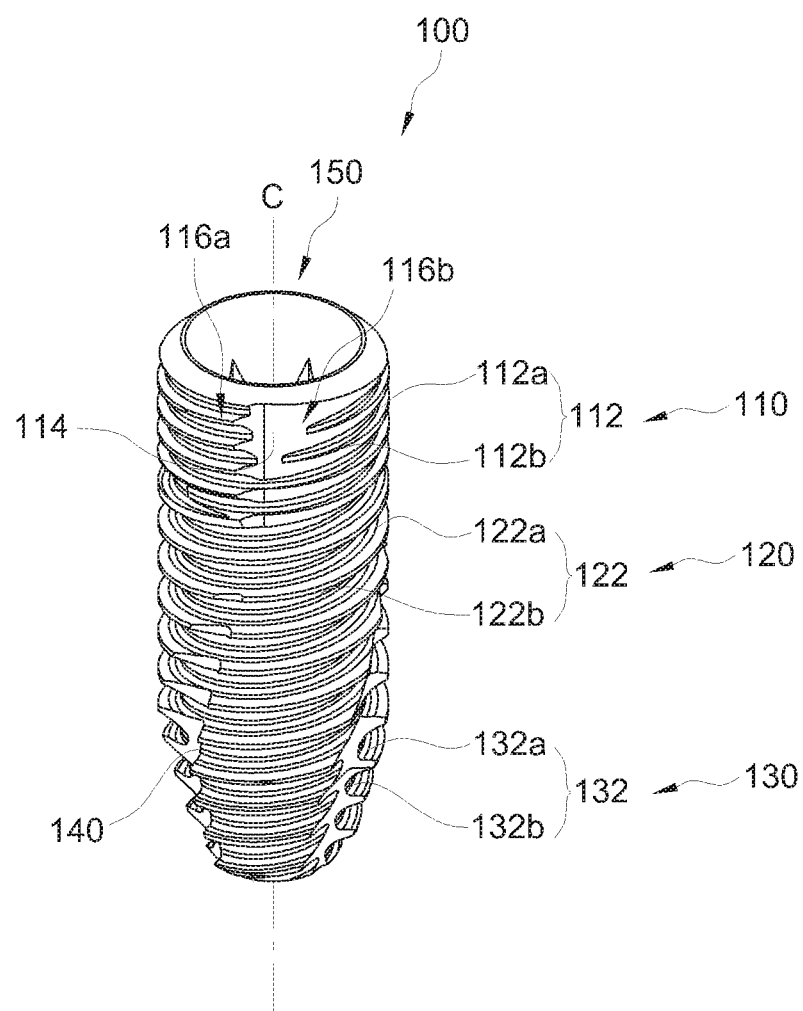
[FIG. 2]

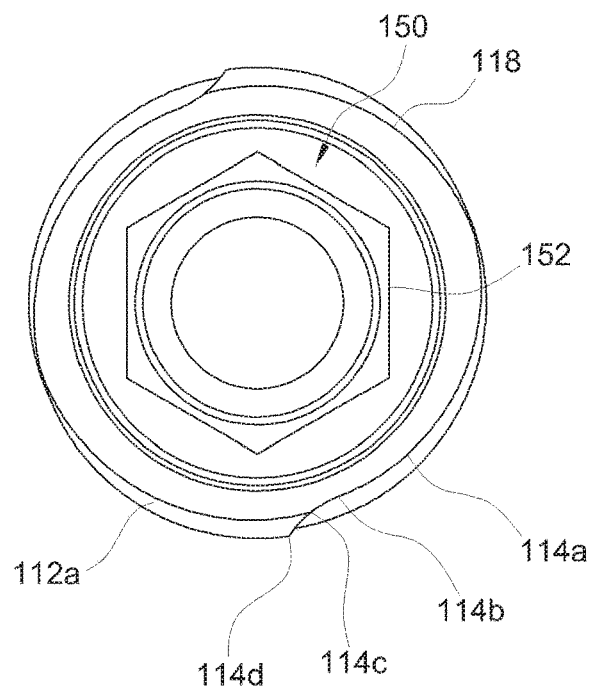
[FIG. 3]
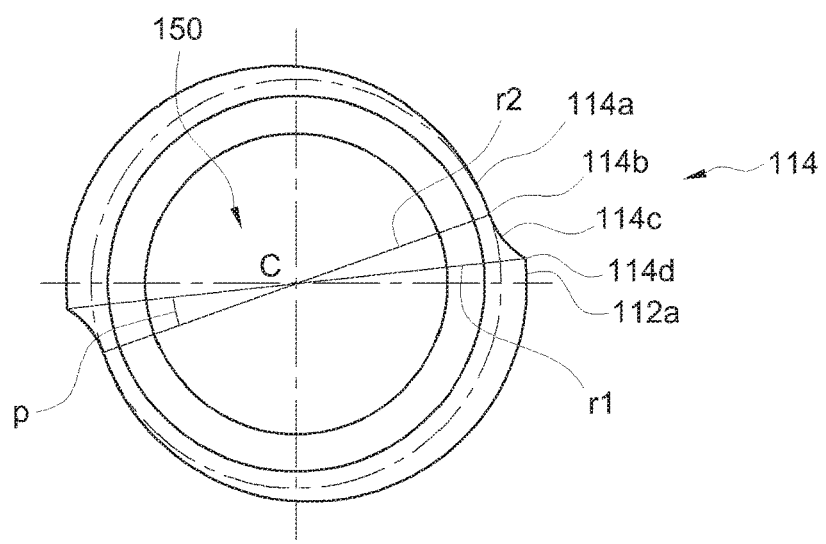
[FIG. 4A]

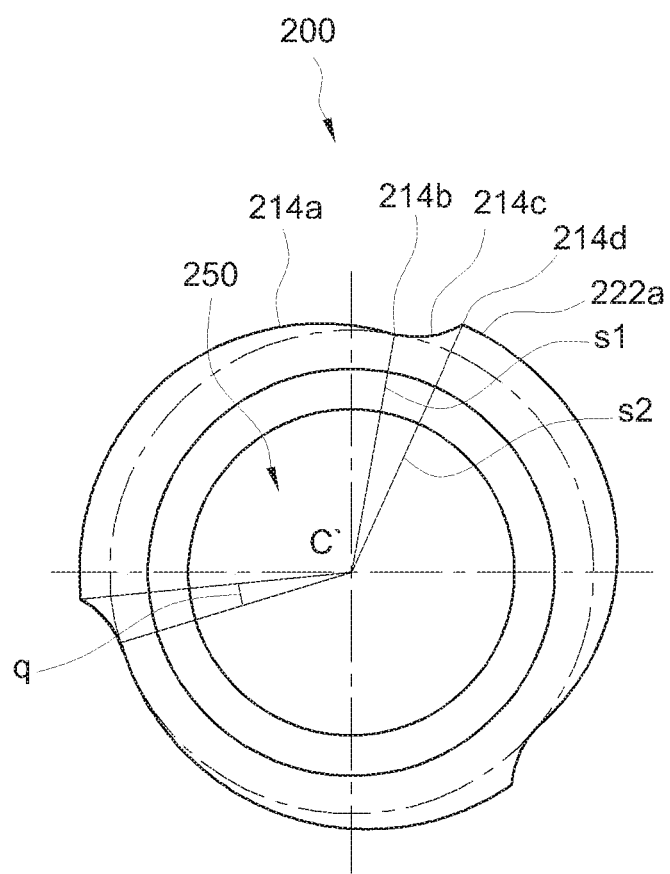
[FIG. 4B]

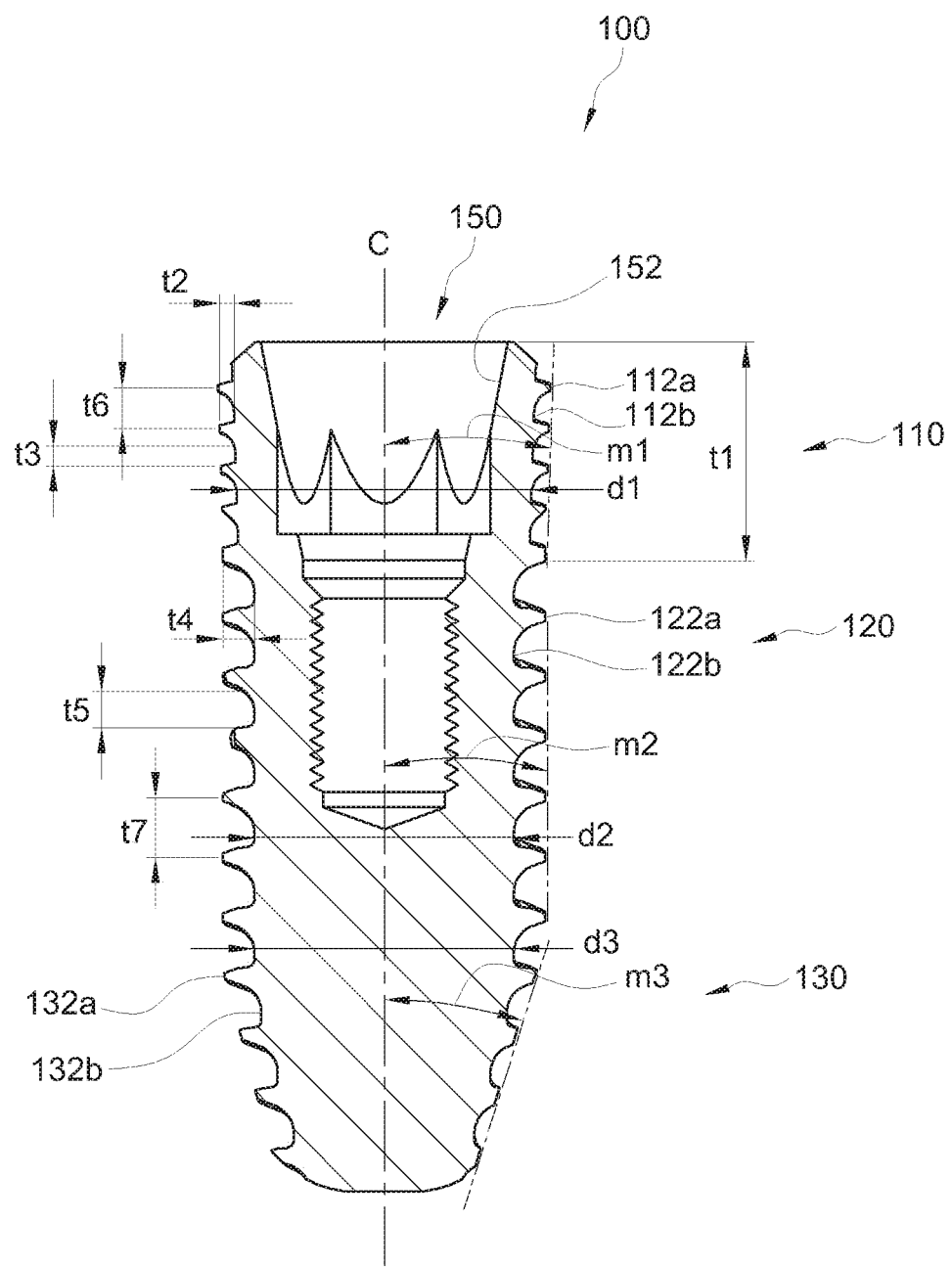
[FIG. 5]

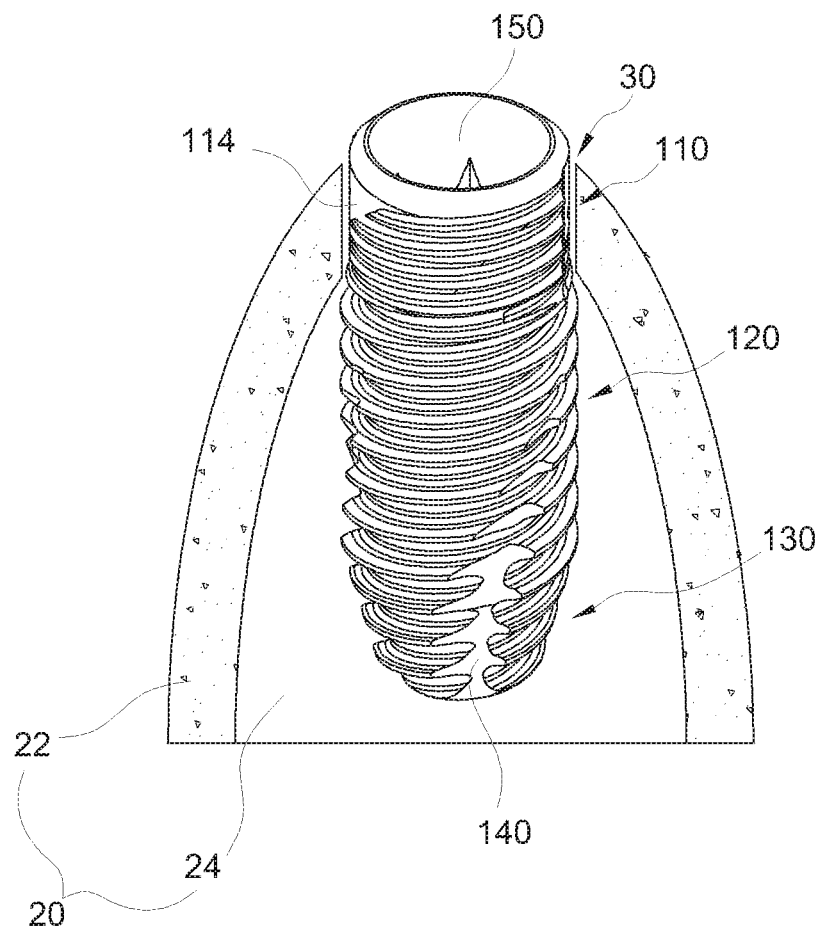
[FIG. 6A]

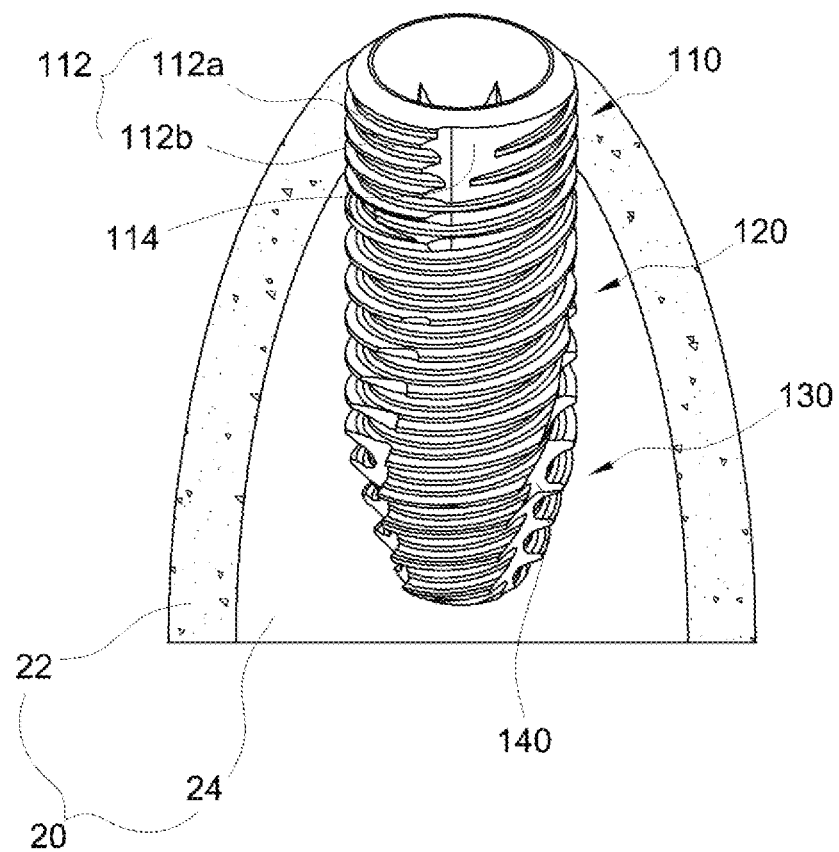
[FIG. 6B]

IMPLANT FIXTURE

CROSS-REFERENCE TO RELATED APPLICATIONS

This application claims priority to and the benefit of Korean Patent Application No. 10-2016-128462, filed on Oct. 5, 2016, the disclosure of which is incorporated herein by reference in its entirety.

BACKGROUND

Field of the Invention

The present invention relates to an implant fixture used during a prosthesis treatment, and more particularly, to an implant fixture for preventing bone resorption and bone compression by minimizing stress on a hard portion of bone tissue.

Description of the Related Art

A screw type of fixture used in dentistry is inserted into bone tissue to form an artificial tooth root. When a fixture is inserted into bone tissue and combined with peripheral bone tissue, an abutment is coupled onto the fixture, and a prosthesis, which is an artificial tooth, is connected to the abutment. Such a fixture is made of a metal or the like fusible with peripheral bone tissue, has screw threads which are formed from an upper end to a lower end of an outer circumferential surface of a body portion of the fixture, and is used as a fixing member for fixing an orthopedic prosthesis as well as a dental prosthesis to a bone.

Meanwhile, bone tissue into which a fixture is inserted and implanted includes a cortical bone and a cancellous bone. The cancellous bone is relatively soft bone tissue of a bone, and the cortical bone is harder than the cancellous bone and is generally formed as a relatively thin film surrounding the cancellous bone. When the fixture is inserted into bone tissue, a length of a portion in contact with the cancellous bone is greater than that of a portion in contact with the cortical bone.

An implant fixture 10 used in a dental treatment in the related art includes a head portion 12 having a hole into which a rotary tool is inserted in the center thereof, and a body portion 14, which is provided to be tapered below the head portion 12 and has screw threads 16 which are formed on an outer circumferential surface thereof, as illustrated in FIG. 1.

Bone resorption is one of problems occurring when the implant fixture 10 in the related art is inserted into an alveolar bone of a human body. Bone resorption refers to a phenomenon in which bone tissue into which a fixture is implanted is degraded while an amount of peripheral bone tissue is reduced. Such bone resorption may inhibit stability of a prosthesis by weakening a fixing force of the fixture and may result in damage to the prosthesis.

Biological causes of the bone resorption have not yet been clearly identified. However, since stress acting on bone tissue adjacent to a fixture is non-uniformly distributed, bone resorption has been recognized as being promoted by both over stimulation and low stimulation due to stress concentration. Therefore, it is necessary to uniformly distribute stress in order to prevent bone resorption and promote osseointegration between a fixture and bone tissue.

That is, since the implant fixture 10 in the related art concentrates relatively more stress on a cortical bone, which is a hard portion of bone tissue, bone resorption occurs more frequently in the cortical bone. However, as a pitch of the screw thread 16 and a difference between an outer diameter of the screw thread 16 and an inner diameter thereof (an outer diameter of a screw valley) are increased, partial concentration of stress on an individual screw thread is increased while a fixing force of the fixture is increased.

Since the screw threads 16 of the implant fixture 10 in the related art are formed to be the same as those of a triangular screw or a trapezoidal screw throughout the body portion 14, an imbalance of overall stress in which stress is relatively concentrated on the cortical bone compared to the cancellous bone occurs. Since bone resorption is caused much more in the cortical bone than in the cancellous bone due to such an imbalance of stress on the entire implant fixture 10 in the related art, the bone resorption in the cortical bone adversely affects an appearance of a prosthesis as well as a stability of the prosthesis. Therefore, a demand for reducing the stress concentrated on the cortical bone or preventing the bone resorption in the cortical bone by distributing the stress to the cancellous bone has arisen.

SUMMARY

The present invention is directed to an implant fixture capable of preventing bone resorption and bone compression and enhancing a fixing force by minimizing stress on a hard portion of bone tissue, for example, a cortical bone or the like.

The scope of the present invention is not limited to the above-described object, and other unmentioned objects may be clearly understood by those skilled in the art from the following descriptions.

According to an aspect of the present invention, there is provided an implant fixture. The implant fixture includes a first area portion including a plurality of first screw portions configured to correspond to a cortical bone during implantation in bone tissue and have a first ridge portion and a first bottom portion which are formed to have a spiral shape and alternately disposed in a direction of a central axis, and a plurality of non-screw portions provided between adjacent first screw portions and including a continuous surface having a smaller radius at a terminal end of a first screw portion of one side than a radius of the first bottom portion with respect to the central axis, wherein the radius gradually increases toward a beginning end of a first screw portion of another side, and a second area portion positioned below the first area portion and configured to correspond to a cancellous bone of the bone tissue during the implantation in the bone tissue.

In another embodiment, the continuous surface may have a greater curvature at the terminal end of the first screw portion of the one side than a curvature of the first screw portion, wherein the curvature gradually decreases toward the beginning end of the first screw portion of the another side.

In still another embodiment, the continuous surface may be processed and may converge in consideration of a radius of the first screw portion with respect to the central axis at the beginning end of the first screw portion of the another side, and may be continuously connected to the beginning end of the first screw portion.

In yet another embodiment, the first ridge portion may be processed in a spiral shape having a radius which gradually increases from the continuous surface toward the terminal end of the first screw portion of the another side with respect to the central axis.

In yet another embodiment, the first area portion may further include an extended portion positioned to correspond to an upper portion of an uppermost first ridge portion in each of the first screw portions, configured to extend from the non-screw portion adjacent to the beginning end of the first screw portion to an upper portion of the terminal end of the first screw portion, and having a radius which is greater than that of the non-screw portion at the beginning end, is continuously processed from the non-screw portion, and gradually increases toward the terminal end. Here, each of the uppermost first ridge portions may have a radius which gradually increases from the beginning end toward the terminal end and is greater than that of a corresponding extended portion at the terminal end with respect to the central axis.

In yet another embodiment, the continuous surface may be a curved portion, and each of the non-screw portions may further include a reverse curved portion which is processed in a curved direction opposite to the curved portion between a first ridge portion positioned at the terminal end of the first screw portion of the one side and the curved portion and includes an edge having the same radius as that of the first ridge portion positioned at the terminal end with respect to the central axis.

In this case, the curved portion and the reverse curved portion may have curved directions opposite to each other based on an inflection site, an angle between the edge of the reverse curved portion and the inflection site based on the central axis may range from 5 degrees to 10 degrees, and a ratio between a radius of the inflection site with respect to the central axis and a radius of the edge of the reverse curved portion adjacent to an uppermost first ridge portion of the first screw portion of the one side with respect to the central axis may range from 0.85 to 0.95.

In yet another embodiment, the first ridge portion may be processed to enter the non-screw portion more toward a lower portion thereof along the direction of the central axis.

In yet another embodiment, a maximum height of each of the non-screw portions may range from 2.5 mm to 3.0 mm, and the non-screw portions may be disposed to be spaced to have the same angle from each other.

Details of other embodiments are included in detailed descriptions and the drawings.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a perspective view of a conventional implant fixture;

FIG. 2 is a perspective view of an implant fixture according to one embodiment of the present invention;

FIG. 3 is a plan view of an implant fixture according to one embodiment of the present invention;

FIG. 4A is a schematic diagram illustrating an upper portion of an implant fixture according to one embodiment of the present invention, and FIG. 4B is a schematic diagram illustrating an upper portion of an implant fixture according to another embodiment of the present invention;

FIG. 5 is a cross-sectional view of an implant fixture according to one embodiment of the present invention; and FIGS. 6A and 6B are views illustrating various side surfaces in a state in which an implant fixture is implanted in bone tissue.

DETAILED DESCRIPTION

Hereinafter, embodiments of the present invention will be described in detail with reference to the accompanying drawings and the following detailed embodiments. However, the present invention is not limited to the embodiments described herein, and may be implemented in a different form. The embodiments described herein are provided to thoroughly complete the disclosure and fully convey the concept of the present invention to those skilled in the art. Like numbers refer to like elements throughout this specification. Meanwhile, terms used in this specification are considered in a descriptive sense only and not for purposes of limitation. In this specification, the singular forms include the plural forms unless the context clearly indicates otherwise. It will be understood that the terms "comprise" and/or "comprising" when used herein, specify some stated components, steps, operations and/or elements, but do not preclude the presence or addition of one or more other components, steps, operations and/or elements.

Further, expressions of a positional relationship used in this specification, for example, an upper portion, a lower portion, a left side, a right side, and the like, are used herein for convenience of description, and the positional relationship described herein may be interpreted in reverse when reversely viewing the drawings illustrated in this specification.

Hereinafter, implant fixtures according to embodiments of the present invention will be described in detail with reference to FIGS. 2 to 5.

FIG. 2 is a perspective view of an implant fixture according to one embodiment of the present invention and FIG. 3 is a plan view of an implant fixture according to one embodiment of the present invention. FIG. 4A is a schematic diagram illustrating an upper portion of an implant fixture according to one embodiment of the present invention, and FIG. 4B is a schematic diagram illustrating an upper portion of an implant fixture according to another embodiment of the present invention. FIG. 5 is a cross-sectional view of an implant fixture according to one embodiment of the present invention.

An implant fixture 100 according to the present embodiment is inserted into bone tissue 20 (see FIG. 6A) including a cortical bone 22 (see FIG. 6A) and a cancellous bone 24 (see FIG. 6A) to form an artificial tooth root. Such an implant fixture 100 may have a substantially cylindrical shape, and may include a ridge portion having a spiral shape which is formed on an outer circumferential surface thereof. While the implant fixture 100 rotates along a central axis C and is implanted into the cortical bone 22 and the cancellous bone 24, the implant fixture 100 forms a screw groove in an inner circumferential surface of an implantation hole which is previously provided in the bone tissue 20 by a drill and is implanted. In this case, titanium may be generally used as a material used in the implant fixture 100, and it is also possible to use different kinds of metal materials as long as a material is not rejected by a human body.

The implant fixture 100 according to one embodiment of the present invention may include a first area portion 110 corresponding to the cortical bone 22 during implantation in the bone tissue 20, a second area portion 120 corresponding to the cancellous bone 24 of the bone tissue 20 during the implantation, a third area portion 130 which is disposed below the second area portion 120 and is tapered, cutting portions 140 which cross from the second area portion 120 to the third area portion 130, and a coupling portion 150 in which a fastening screw is coupled to a lower end of an abutment (not illustrated).

The first area portion 110, which is a portion which is mostly inserted into the cortical bone 22 when the implant fixture 100 is inserted, may form an upper portion of the implant fixture 100, and a portion of a lower portion of the first area portion 110 may be implanted into the cancellous bone 24. The first area portion 110 includes a plurality of first screw portions 112 each including a first ridge portion 112a and a first bottom portion 112b which are processed in a spiral shape on an outer circumferential surface of the first area portion 110, and the first ridge portion 112a and the first bottom portion 112b are alternately disposed along a direction of the central axis C of the implant fixture 100. The plurality of first screw portions 112 may be disposed on the outer circumferential surface of the first area portion 110 along the direction of the central axis C to be spaced to have a predetermined angle, for example, the same angle, from each other.

The first area portion 110 includes a non-screw portion 114 which is provided between adjacent first screw portions 112 on the outer circumferential surface of the first area portion 110 along a rotational direction of the central axis C. The non-screw portion 114 may include a curved portion 114a which is a flat and continuous surface so that the first ridge portion 112a and the first bottom portion 112b are not formed therein at all. A plurality of non-screw portions 114 may be arranged between adjacent first screw portions 112 to be spaced to have the same angle from each other. For example, when two non-screw portions 114 are provided as illustrated in FIGS. 2 to 4A, the non-screw portions 114 may be disposed to oppose each other at 180 degrees intervals, and when three non-screw portions 114 are provided as illustrated in FIG. 4B, the non-screw portions 114 may be disposed to be spaced 120 degrees apart from each other. In the present embodiment, two or three non-screw portions 114 are illustrated as being provided, but a larger number of the non-screw portions 114 than the illustrated number of the non-screw portions 114 may be provided as long as conditions of a reduction of stress on the cortical bone 22 and a sufficient fixing force of the implant fixture 100 are satisfied.

The curved portion 114a of the non-screw portion 114 is formed to have a smaller radius at a terminal end 116a of the first screw portion 112 of one side than a radius of the first bottom portion 112b with respect to the central axis C, and the radius gradually increases toward a beginning end 116b of the first screw portion 112 of another side. In this case, as illustrated in FIG. 2, the terminal end 116a of the first screw portion 112 is an end in the vicinity of a cut portion of the first screw portion 112 positioned at a left side of the non-screw portion 114 and the beginning end 116b of the first screw portion 112 is an end in the vicinity of a portion at which the first screw portion 112 positioned at a right side of the non-screw portion 114 begins. Further, the curved portion 114a may have a greater curvature at the terminal end 116a of the first screw portion 112 of one side than a curvature of the first screw portion 112, and the curvature gradually decreases toward the beginning end 116b of the first screw portion 112 of the another side in order to meet a condition of the above-described radius. Also, the first ridge portion 112a may be processed in a spiral shape having a radius which gradually increases from the continuous surface (the non-screw portion 114) toward the terminal end 116a of the first screw portion 112 of the another side with respect to the central axis C. As shown in FIGS. 2 to 4a, the radius of the curved portion 114a abutting the terminal end 116a of the first screw portion 112 of one side is smaller than that of the first bottom portion 112b adjacent to the beginning end 116b of the first screw portion 112 of another side, and then also smallest in outer circumferential plane of the first area portion 110.

Detailed explanations of the non-screw portion 114 and the first screw portion 112 will be described later.

The second area portion 120 is disposed to be integrally coupled to the lower portion of the first area portion 110, but the present invention is not limited thereto, and another structure may be disposed between the first and second portions 110 and 120. The second area portion 120 is a portion which is mostly inserted into the cancellous bone 24, and a portion of an upper portion of the second area portion 120 may be implanted into the cortical bone 22. The second area portion 120 includes a second screw portion 122 including a second ridge portion 122a and a second bottom portion 122b which are processed in a spiral shape on an outer circumferential surface of the second area portion 120, and the second ridge portion 122a and the second bottom portion 122b are alternately disposed along the direction of the central axis C of the implant fixture 100.

The second screw portion 122 may be continuously connected to the first screw portion 112 as illustrated in FIG. 2. Accordingly, the implant fixture 100 may be smoothly inserted into the bone tissue 20 without a sharp increase in implantation torque.

The third area portion 130 is disposed below the second area portion 120 and forms a lowermost end of the implant fixture 100. The third area portion 130 is an entrance portion which is initially inserted into the bone tissue 20 to form female screw threads inside the bone tissue 20. The third area portion 130 includes a third screw portion 132 including a third ridge portion 132a and a third bottom portion 132b which are processed in a spiral shape on an outer circumferential surface of the third area portion 130, and the third ridge portion 132a and the third bottom portion 132b are alternately disposed along the direction of the central axis C of the implant fixture 100.

The cutting portions 140 which cross from the second screw portion 122 to the third screw portion 132 may be processed and provided along an outer circumferential surface of the implant fixture 100 at equal intervals. The cutting portions 140 which cross an upper portion of the second screw portion 122 may have a shape that extends to an upper portion thereof so as not to be parallel to the central axis C, and specifically, may have a shape upwardly inclined while being wound in a spiral shape. It is possible to easily migrate from the third area portion 130 to the second area portion 120 by the cutting portions 140 which cross the second screw portion 122.

Specifically, the cutting portions 140 formed in the second screw portion 122 may be formed to have a depth smaller than a height t4 (see FIG. 5) of the second ridge portion 122a, and when the depth of the cutting portion 140 is greater than the height t4 of the second ridge portion 122a, the implant fixture 100 may not be able to be smoothly inserted into the bone tissue 20.

Further, the cutting portions 140 which cross the third screw portion 132 may contribute to facilitating insertion of the third area portion 130 into the bone tissue 20, and may extend vertically upward from a lower end thereof to be connected to the cutting portions 140 of the second screw portion 122. Specifically, the cutting portions 140 processed in the third screw portion 132 may extend upwardly in parallel to the central axis C, and may be processed to be deeper than the third bottom portion 132b. The cutting portions 140 are processed in this way so that the cutting portions 140 positioned at the lowermost end of the implant fixture 100 may easily cut a bone abutting the previously provided implantation hole of the bone tissue 20.

As the cutting portions 140 formed on the second screw portion 122 are formed to have a shape different from that of the cutting portions 140 formed on the third screw portion 132, peripheral bone tissue roughly cut by the cutting portion 140 corresponding to the third screw portion 132 may be finely cut by the cutting portion 140 of the second screw portion 122 having a spiral shape, and thus a surface roughness of a peripheral bone may be improved. That is, since the cutting portion 140 of the second screw portion 122 rotates, peripheral bone tissue roughened by the cutting portion 140 of the third screw portion 132may be smoothly processed.

As can be seen in FIG. 5, the coupling portion 150 may include a hole 152 having a polygonal shape which accommodates a lower end of an abutment (not illustrated) and a fastener which is disposed below the hole 152 and processed to have a female screw so as to be coupled to a fastening screw of the abutment. Since the hole 152 is formed to have a polygonal shape, a coupling direction of the abutment may be easily identified and, at the same time, the lower end of the abutment may be stably fixed. Further, since a side wall of the hole 152 has a width which increases in an upward direction, the abutment is easily guided to the fastening portion, and to this end, the side wall of the hole 152 may be processed to recede from the central axis C in the upward direction to be formed to have an angle ranging from about 8 degrees to about 15 degrees with respect to the central axis C.

Hereinafter, the first to third area portions 110 to 130 will be described in more detail, a portion of the non-screw portion 114, which is illustrated in FIG. 2, will be mainly described, and these descriptions are identically applied to all of the non-screw portions 114 illustrated in FIGS. 4A and 4B.

Referring to FIG. 2, the first ridge portion 112a and the first bottom portion 112b of the first area portion 110 may be processed to enter the non-screw portions 114 more in a downward direction relative to the direction of the central axis C in order to reduce stress on an upper side of the cortical bone 22 and secure a fixing force at the cortical bone 22 in the vicinity of the cancellous bone 24.

Further, the curved portion 114a may processed to converge in consideration of the radius of the first screw portion 112, for example, the radius of the first ridge portion 112a with respect to the central axis C at the beginning end 116b of the first screw portion 112 of the another side, so that the first ridge portion 112a which enters the non-screw portions 114 more toward a lower portion of the first area portion 110, is smoothly inserted into the cortical bone 22 without sharply increasing an implantation torque, and may be continuously connected to the beginning end 116b of the first screw portion 112.

In addition, the curved portion 114a and the first ridge portions 112a continuously connected to the curved portion 114a may be formed to have a radius which gradually increases from the curved portion 114a to the terminal end 116a of the first ridge portion 112a positioned opposite a reverse curved portion 114c with respect to the central axis C in order to reduce stress on the cortical bone 22, be smoothly implanted in the cortical bone 22, and secure a fixing force at the cortical bone 22 as illustrated in FIG. 4A which schematically illustrates a state of connecting the curved portion 114a to the uppermost first ridge portion 112a. Similarly, in FIG. 4B, which illustrates another embodiment of the present invention, the curved portion 214a and the first ridge portions 222a may also be formed to have a radius which gradually increases from a curved portion 214a to the terminal end of the first ridge portion 222a of the first screw portion positioned opposite a reverse curved portion 214c with respect to the central axis C'.

In the present embodiment, the first screw portion 112 enters the curved portion 114a more toward a lower portion of the curved portion 114a, and a radius of the curved portion 114a adjacent to the beginning end 116b of the first ridge portion 112a is configured to be the same as that of the first ridge portion 112a at the corresponding position, but the present invention is not limited thereto, and the above radiuses may be the same as each other as long as reduction of stress, securing of a fixing force, and smooth insertion of the cortical bone 22 are met so that positions at which the first ridge portions 112a enter the non-screw portions 114 are parallel to each other along the central axis C. Further, when the curved portion 114a is connected to the beginning end 116b of the first ridge portion 112a and has a smooth curved surface, the radius of the curved portion 114a may be smaller than a radius of the beginning end 116b of the first ridge portion 112a.

Meanwhile, as illustrated in FIGS. 3 and 4A, each of the non-screw portions 114 may include the curved portion 114a and the reverse curved portion 114c which is formed in a curved direction different from that of the curved portion 114a based on an inflection site 114b and includes an edge 114d corresponding to the terminal end 116a of the first screw portion 112 of one side. The curved portions 114a and the reverse curved portions 114c, which are opposite to each other, may be arranged to be symmetrical relative to the central axis C as the origin.

As described above, in the terminal end 116a of the first screw portion 112 of one side, the curved portion 114a of the non-screw portion 114 is formed to have a radius which is smaller than that of the first bottom portion 112b with respect to the central axis C, and a curvature which is greater than that of the first screw portion 112. The radius of the curved portion 114a abutting the terminal end 116a of the first screw portion 112 of one side is smaller than that of the first bottom portion 112b adjacent to the beginning end 116b of the first screw portion 112 of another side, and then also smallest in outer circumferential plane of the first area portion 110. Further, the curved portion 114a may be processed to have a radius which gradually increases and a curvature which gradually decreases toward the beginning end 116b of the first screw portion 112 of the another side.

The reverse curved portion 114c may be processed between the first ridge portion 112a positioned at the terminal end 116a of the first screw portion 112 of one side and the curved portion 114a in a curving direction opposite to that of the curved portion 114a for sufficient separation from the cortical bone 22 and smooth implantation with the curved portion 114a, and may have the edge 114d having the same radius as a radius r1 of the first ridge portion 112a which is positioned at the terminal end 116a with respect to the central axis C. The present invention is not limited thereto, and the reverse curved portion 114c may be omitted and the terminal end 116a of the first ridge portion 112a is sharply cut to be inclined, for example vertical, to the first ridge portion 112a positioned at the terminal end 116a toward the central axis C, and thus the terminal end 116a of the first ridge portion 112a may be connected to the curved portion 114a.

As illustrated in FIG. 4A, an angle p between the edge 114d of the reverse curved portion 114c and the inflection site 114b relative to the central axis C may be formed to range from 5 degrees to 10 degrees. When the angle p is less than 5 degrees, a sufficient space from the cortical bone 22 may not be secured, and when the angle p is more than 10 degrees, the implantation may not be smooth and a fixing force may be insufficient.

Further, as illustrated in FIG. 5, when an uppermost first ridge portion 112a is greater than a first ridge portion 112a positioned therebelow by having an inclined angle between an alternate long and short dash line which connects the first ridge portions 112a and the central axis C, a ratio r2/r1 between a radius r2 of the inflection site 114b with respect to the central axis C and the radius r1 of the edge 114d of the reverse curved portion 114c adjacent to the uppermost first ridge portion 112a of the first screw portion 112 of one side with respect to the central axis C may range from 0.85 to 0.95. When the ratio r2/r1 is more than 0.95, sufficient spacing from the cortical bone 22 may not be secured, and when the ratio r2/r1 is less than 0.85, the implantation may not be smooth and a fixing force may be insufficient.

Similarly, in FIG. 4B which illustrates another embodiment of the present invention, an angle q between an edge 214d of the reverse curved portion 214c and an inflection site 214b may also be formed to range from 5 degrees to 10 degrees, and a ratio s2/s1 between a radius s2 of the inflection site 214b and a radius s1 of the edge 214d of the reverse curved portion 214c adjacent to the uppermost first ridge portion may also range from 0.85 to 0.95.

Referring again to FIG. 2, the first area portion 110 may further include an extended portion 118 which is positioned to correspond to an upper portion of the uppermost first ridge portion 112a in each of the first screw portions 112 and extends from the non-screw portion 114 adjacent to the beginning end 116b of the first screw portion 112 to the terminal end 116a of the first screw portion 112. The extended portion 118 may have a radius which is greater than that of the non-screw portion 114 at the beginning end 116b of the first screw portion 112, is continuously processed from the non-screw portion 114, and gradually increases toward the terminal end 116a so that gums smoothly grow on and optimally cover the upper portion of the implant fixture 100 after an implant treatment. In this case, each of the uppermost first ridge portions 112a has a radius which gradually increases from the curved portion 114a toward the terminal end 116a positioned opposite to the reverse curved portion 114c, and is greater than that of the corresponding extended portion 118 at the terminal end 116a as described above. That is, since the radius of the extended portion 118 is smaller than that at the terminal end 116a of the first screw portion 112, the first screw portion 112 may be strongly fixed to the cortical bone 22 and the gums may smoothly grow and optimally cover the upper portion of the implant fixture 100.

Sizes, relative angles, and the like of the first to third portions will be described with reference to FIG. 5.

As illustrated in FIG. 2, when the first ridge portions 112a enters the non-screw portion 114 more toward a lower portion of the non-screw portion 114, a maximum height t1 of the curved portion 114a adjacent to the reverse curved portion 114c at each of the non-screw portions 114 may range from 2.5 mm to 3.0 mm to sufficiently correspond to the cortical bone 22. A height of the first area portion 110 may be substantially the same as the maximum height t1 of the non-screw portion 114, and when the first ridge portions 112a enters the non-screw portion 114 at the same position, a height of the curved portion 114a may range from 2.5 mm to 3.0 mm to be uniformly formed from the inflection site 114b to the beginning end 116b of the first screw portion 112.

A height t2 of the first ridge portion 112a of the first screw portion 112 may be formed to be smaller than a height t4 of the second ridge portion 122a of the second screw portion 122, a pitch t6, which is a distance between adjacent first ridge portions 112a, may be formed to be smaller than a pitch t7, which is a distance between adjacent second ridge portions 122a. The first screw portion 112 is formed to have a size different from that of the second screw portion 122 in this way due to a difference between characteristics of bones into which each portion is implanted. For example, the first screw portion 112 inserted into the hard cortical bone 22 forms dense screw threads in order to prevent stress on a contact portion with the cortical bone 22 from being concentrated, and thus overall stress may be uniformly distributed to the peripheral bone tissue 20. Further, the second screw portion 122 inserted into the relatively soft cancellous bone 24 may increase a size of a captured portion of the peripheral bone tissue 20, and thus a fixing force may be sufficiently secured.

Further, a width t3 of the first bottom portion 112b may be formed to be smaller than a width t5 of the second bottom portion 122b. Alternatively, when the width t3 is greater than the width t5, the first screw portion 112 may not secure sufficient supporting force with the peripheral bone tissue 20 and may cause excessive stress on the peripheral bone tissue 20.

In addition, the first ridge portions 112a and the first bottom portions 112b may have an outer diameter which increases toward upper portions thereof so that an angle m1 between the alternate long and short dash line which connects the first ridge portions 112a and the central axis C ranges from 0.2 degree to 2 degrees. Thus, since the outer diameter of the first area portion 110 increases toward the upper portion thereof, pressure applied by the implant fixture 100 during implantation in bone tissue may be gradually increased, and accordingly, the implant fixture 100 may be securely fixed to the bone tissue 20.

An angle m2 between an alternate long and short dash line which connects the second ridge portions 122a and the central axis C may be 0 degrees to be disposed in parallel to each other, and thus may prevent excessive insertion torque and damage to bone tissue. An angle m3 between an alternate long and short dash line which connects the third ridge portions 132a and the central axis C may be formed to be greater than the angle between the first ridge portions 112a and the central axis C in order to be easily inserted into the bone tissue 20.

Further, outer diameters d2 of all of the second bottom portions 122b may be formed to be smaller than outer diameters d1 of all of the first bottom portions 112b. By being formed like this, when the implant fixture 100 is inserted into the peripheral bone tissue 20 from the second area portion 120 to the first area portion 110, sufficient pressure may be applied to the adjacent bone tissue 20 and an initial fixing force may be sufficiently secured.

Meanwhile, the first screw portion 112 and the second screw portion 122 may have a multiple lines. That is, a screw thread having two lines or more is formed. Here, a screw having n lines represents a distance by which the ridge portion is moved in the direction of the central axis C when rotated around the implant fixture 100 once relative to a ridge portion of a screw portion. In other words, the screw having n lines is understood as the number n of lines per lead.

FIGS. 6A and 6B are views illustrating various side surfaces in a state in which an implant fixture is implanted in bone tissue.

When the implant fixture 100 passes through the cortical bone 22 and is inserted into the cancellous bone 24, the non-screw portion 114 corresponding to the cortical bone 22 is formed to have a radius that is smaller than that of the first bottom portion 112b of the first screw portion 112 adjacent to the edge 114d, the reverse curved portion 114c is connected to the curved portion 114a in a curved direction different therefrom to have a predetermined angle and a ratio between radiuses of an inflection site 114b and the edge 114d, and thus the implant fixture 100 is inserted into the bone tissue 20 in a state in which a gap 30 between the non-screw portion 114 and the cortical bone 22 is maintained as illustrated in FIG. 6A.

As can be seen in FIG. 6B, the first ridge portions 112a have radiuses which increase and are continuously connected to the non-screw portion 114, the reverse curved portion 114c is connected to the curved portion 114a to have a predetermined angle and a ratio between radiuses of the inflection site 114b and the edge 114d, the first ridge portions 112a are formed to have a height and a pitch which are smaller than those of the second ridge portions 122a, and thus the first ridge portions 112a are smoothly implanted into the cortical bone 22 and are optimally fixed to the cortical bone 22.

That is, according to the present embodiment, a mechanical structure in which stress is minimized is implemented in the first area portion 110 during implantation in the bone tissue 20 so that a larger volume of bone is allowed in the first area portion 110 of the implant fixture 100 corresponding to a hard portion of the bone tissue 20, and thus bone resorption and bone compression may be prevented while sufficiently securing a sufficient fixing force to the bone tissue 20.

According to the present invention, a mechanical structure in which stress is minimized is implemented in an area portion corresponding to a hard portion during implantation in bone tissue so that a larger volume of bone is allowed in an area portion of a fixture corresponding to a hard portion of the bone tissue, and thus bone resorption and bone compression can be prevented.

While the present invention has been described above in detail with reference to representative embodiments, it may be understood by those skilled in the art that the embodiments may be variously modified without departing from the scope of the present invention. Therefore, the spirit and scope of the invention are defined not by the detailed description of the invention but by the appended claims, and encompass all modifications and equivalents that fall within the scope of the appended claims.

The invention claimed is:

1. An implant fixture comprising:
an elongate tubular body having a first area portion and a second area portion;
the first area-portion including
a plurality of first screw portions for implantation into a cortical bone,
each of the plurality first screw portions comprising a first ridge portion and a first bottom portion, the first ridge portion extending radially outward from the first bottom portion, the first ridge portion and the first bottom portion of the plurality of first screw portions disposed alternately in a direction of a central axis of the implant fixture,
the plurality of first screw portions arranged in a spiral shape on the elongate tubular body, the plurality of first screw portions having a beginning end and a terminal end, and
a plurality of non-screw portions provided between circumferentially adjacent first screw portions, the plurality of non-screw portions including a continuous surface disposed between the circumferentially adjacent first screw portions,
the plurality of first screw portions comprising a first screw portion and an adjacent first screw portion, adjacent to the first screw portion along the circumference of the elongate tubular body, and separated from the first screw portion by a first non-screw portion from the plurality of non-screw portions,
the continuous surface extending from a terminal end of the first screw portion to a beginning end of the adjacent first screw portion, the continuous surface comprising a curved portion and reverse curved portion, the reverse curved portion extending from the terminal end of the first screw portion to an inflection site in the continuous surface, the curved portion extending from the inflection site to the beginning end of the adjacent first screw portion, the curved portion curved in the same direction as the first screw portions, the reverse curved portion curved in a direction opposite to the curve of the curved portion,
a radius of the inflection site with respect to the central axis, the radius of the inflection site being smaller than a radius of the first bottom portion of the first screw portion with respect to the central axis,
wherein the radius of the curved portion gradually increases from the inflection site to the beginning end of the adjacent first screw portion, and
wherein the curved portion converges to match curvature and radius of, and is continuously connected to, the beginning end of the adjacent first screw portion; and
the second area portion positioned below the first area portion, the second area portion for implantation into a cancellous bone.

2. The implant fixture of claim 1, wherein the curved portion has a greater curvature than a curvature of the terminal end of the first screw portion, and wherein the curvature gradually decreases from the inflection site toward the beginning end of the adjacent first screw portion.

3. The implant fixture of claim 1, wherein the first ridge portion has a radius with respect to the central axis, and wherein the radius increases from the beginning end of the first screw portion to the terminal end of the first screw portion.

4. The implant fixture of claim 1, wherein:
an arc angle between an edge of the reverse curved portion coinciding with the terminal end of the first screw portion, and the inflection site, based on the central axis, ranges from about 5 degrees to about 10 degrees.

5. The implant fixture of claim 4, wherein:
a ratio between a radius of the inflection site with respect to the central axis and a radius of the edge of a reverse curved portion adjacent to a first ridge portion of an uppermost first screw portion with respect to the central axis ranges from about 0.85 to about 0.95.

6. The implant fixture of claim 1, wherein the plurality of non-screw portions further comprise a second non-screw portion adjacent to the first non-screw portion along the central axis, the second non-screw portion closer to the second area portion than the first non-screw portion, and the second non-screw portion smaller than the first non-screw portion.

7. The implant fixture of claim 1, wherein a maximum height of each of the non-screw portions along the central axis ranges from about 2.5 mm to about 3.0 mm, and the non-screw portions are disposed symmetrically on a circumference of the elongate tubular body.

8. An implant fixture comprising:
an elongate tubular body having a curved outer profile, the elongate tubular body comprising
a first area portion for implantation into cortical bone, and
a second area portion for implantation into cancellous bone, the first area portion comprising
a plurality of first screw portions arranged in a spiral shape on the curved outer profile,
the plurality of first screw portions comprising
a first screw portion, and
an adjacent first screw portion, which is adjacent to the first screw portion along a circumference of the elongate tubular body, each of the plurality of first screw portions comprising
a first ridge portion extending continuously between a beginning end and a terminal end of corresponding each of the plurality of first screw portions, and
a first bottom portion at a base of the first ridge portion, the first ridge portion extending radially outward from the first bottom portion,
the first ridge portion and the first bottom portion of the plurality of first screw portions disposed alternately along a central axis of the elongate tubular body,
wherein the first ridge portion has a radius with respect to the central axis, the radius increasing from the beginning end of the first screw portion to the terminal end of the first screw portion
a non-screw portion positioned between the first screw portion and the adjacent first screw portion, the non-screw portion comprising a continuous surface between the first screw portion and the adjacent first screw portion,
the continuous surface positioned between a terminal end of the first screw portion and a beginning end of the adjacent first screw portion, the continuous surface comprising
a curved portion having a curve in the same direction as that of the curved outer profile,
a reverse curved portion curved in a direction opposite to the curved portion, and
an inflection site connecting the curved portion and the reverse curved portion,
wherein the reverse curved portion extends to the terminal end of the first screw portion, and the curved portion extends to the beginning end of the adjacent first screw portion,
wherein a radius of the curved portion with respect to the central axis increases from the inflection site to the beginning end of the adjacent first screw portion, and
wherein a portion of the curved portion of the continuous surface at the beginning end of the adjacent first screw portion merges into a first ridge portion of the adjacent first screw portion.

9. The implant fixture of claim 8, wherein a ratio of the radius of the curved portion at the inflection site to a radius of an edge of the terminal end of the first screw portion from the central axis is between about 0.85 to about 0.95.

10. The implant fixture of claim 8, wherein the second portion comprises a second screw portion, wherein the second screw portion is formed as a continuous structure with a first screw portion proximal to the second portion.

11. The implant fixture of claim 8, wherein at least one first screw portion from the plurality of first screw portions spans a complete circumference across the curved outer profile of the implant fixture.

* * * * *